United States Patent
Hollfelder et al.

(10) Patent No.: US 6,720,440 B2
(45) Date of Patent: Apr. 13, 2004

(54) PROCESS FOR THE CHLORINATION OF METHYLSILANES

(75) Inventors: Helmut Hollfelder, Burghausen (DE);
Siegfried Pflaum, Kirchdorf (DE);
Franz Riener, Kirchdorf (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/273,687

(22) Filed: Oct. 18, 2002

(65) Prior Publication Data

US 2003/0088117 A1 May 8, 2003

(30) Foreign Application Priority Data

Nov. 8, 2001 (DE) .......................................... 101 54 943

(51) Int. Cl.$^7$ .................................................. C07F 7/04
(52) U.S. Cl. ...................................................... 556/476
(58) Field of Search .......................................... 556/476

(56) References Cited

U.S. PATENT DOCUMENTS

| | | | |
|---|---|---|---|
| 2,684,974 A | * | 7/1954 | Hatcher et al. ............. 556/476 |
| 3,840,447 A | | 10/1974 | Lücking et al. |
| 4,101,397 A | | 7/1978 | Kötzsch et al. |

FOREIGN PATENT DOCUMENTS

| | | |
|---|---|---|
| DE | 2 150 718 | 4/1973 |
| DE | 26 14 197 | 10/1977 |

OTHER PUBLICATIONS

Cerny, Otakar et al., "Chloromethyltrichlorosilane By Photochemical Chlorination Of Methyltrichlorosilane", English Abstract from STN Database, AN 70: 57998 CA.

English Derwent Abstract AN 1973–24288U [18] Corresponding To DE 2150718.

English Derwent Abstract AN 1977–55816Y [32] Corresponding To DE 2614197.

* cited by examiner

*Primary Examiner*—Peter O'Sullivan
(74) *Attorney, Agent, or Firm*—Brooks Kushman P.C.

(57) ABSTRACT

The invention relates to a process for the chlorination of methylsilanes, which comprises reacting methylsilanes with chlorine in the presence of at least 0.1% by weight of hydrogen chloride, based on the weight of methylsilane of the formula (II), under the action of electromagnetic radiation which induces chlorination, chlorine being used in a substoichiometric amount based on the methylsilane of the formula (II), and the reaction being carried out at temperatures below the boiling point of the methylsilane of the formula (II). The invention further relates to an apparatus suitable for carrying out the chlorination of an industrial scale.

9 Claims, No Drawings

PROCESS FOR THE CHLORINATION OF METHYLSILANES

BACKGROUND OF THE INVENTION

1. Field of the Invention

The invention relates to a process for the chlorination of methylsilanes by reaction of methylsilanes with chlorine in the presence of hydrogen chloride, and to an apparatus suitable for carrying out the process.

2. Background Art

It is known that chloromethylchlorosilanes can be prepared by reaction of methylchlorosilanes with chlorine under the action of high-energy light in a liquid and gaseous phase. On this subject, reference may be made, for example, to DE-A 21 50 718 (Bayer A G, published on Apr. 19, 1973), which discloses a process for the chlorination of methylchlorosilanes by reaction of the starting silanes with chlorine, with the methylsilanes being premixed with chlorine in a first zone and this mixture then being exposed to radiation which triggers the photochemical reaction in a second zone, the photochemical reaction being carried out at below the boiling point of the methylsilane to be chlorinated. DE-A 26 14 197 (Dynamit Nobel A G, published on Oct. 13, 1977) describes the continuous photochlorination of methylsilanes by means of chlorine, with the photochemical reaction being carried out at the boiling point of the reaction mixture.

However, the known processes frequently have serious disadvantages, particularly in respect of economics and their ability to be carried out safely.

SUMMARY OF THE INVENTION

The present invention improves upon the chlorination of methylsilanes by chlorination with a substoichiometric amount of chlorine at a temperature below the boiling point of the methylsilane, in the presence of a minor amount of hydrogen chloride, the chlorination induced by electromagnetic radiation.

DETAILED DESCRIPTION OF THE PREFERRED EMBODIMENT(S)

The present invention provides a process for preparing silanes which contain chloromethyl groups and have the formula

$(Cl_yCH_{3-y})_a(CH_3)_bSiCl_{4-a-b}$ where y is 1, 2 or 3, preferably 1, a is 1, 2, 3, or 4, preferably 1, b is 0, 1, 2 or 3, with the proviso that the sum a+b is 1, 2, 3 or 4, which comprises reacting methylsilanes of the formula

$(CH_3)_{a+b}SiCl_{4-(a+b)}$      (II), with chlorine in the presence of at least 0.1% by weight of hydrogen chloride, based on the weight of methylsilane of the formula (II) used, under the action of electromagnetic radiation which triggers the chlorination, with chlorine being used in a substoichiometric amount based on the methylsilane of the formula (II), the reaction being carried out at temperatures below the boiling point of the methylsilane of the formula (II).

Silanes of the formula (II) which are used in the process of the invention are methyltrichlorosilane, dimethyldichlorosilane, trimethylchlorosilane and tetramethylsilane.

Although not shown by the formulae (I) and (II), the process of the invention can also be carried out using silanes of the formula (II) in which all or some of the methyl groups have been replaced by other alkyl groups, e.g. ethyl radicals, propyl radicals, butyl radicals, etc., but this is not preferred.

In the process of the invention, the molar ratio of methylsilane of the formula (II) to chlorine is preferably above 2.0:1.0, more preferably in the range from 6.0:1.0 to 31.0:1.0.

In the process of the invention, hydrogen chloride is preferably used in an amount of at least 0.2% by weight, based on the weight of methylsilane of the formula (II) used. Hydrogen chloride is more preferably used in the form of a methylsilane saturated with hydrogen chloride at atmospheric pressure and a maximum temperature of 40° C.

The process is preferably carried out at temperatures which are from 5 to 15° C. below the boiling point of the methylsilane of the formula (II), and at the pressure of the surrounding atmosphere, i.e. from about 900 to 1,500 hPa. However, the process of the invention can also be carried out at higher or lower pressures.

In the inventive process, the irradiation is preferably performed employing a wavelength range of from 200 to 800 nm, more preferably from 300 to 400 nm. As a radiation source, it is possible, for example, to employ all sources which have been used hitherto in the photochlorination of methylsilanes. The radiation source can be located within or without the reactor. Examples of lamps which can be used for generating the radiation which triggers the photochemical reaction are UVA fluorescent lamps and intermediate-pressure mercury vapor lamps having predominant emission in the range of from 360 to 370 nm.

The radiation employed according to the invention has a preferred radiation density of 15 Einstein/hm$^2$, as can be used, for example, in plants for the industrial preparation of chloromethylsilanes of the formula (I).

The process of the invention can be carried out continuously or batchwise; a continuous process is particularly preferred and will be described in more detail below.

The process can be carried out in all types of reactors which have been used heretofore for carrying out continuous reactions, for example tube reactors, loop reactors and stirred vessels. The reactors used are preferably tube reactors and loop reactors, with tube reactors being particularly preferred. Depending on the reactor type selected, chlorinated reaction products can, if desired, be recirculated to the photochemical reactor. For example, total recirculation of chlorinated reaction products is possible in a loop reactor, while the chlorinated reaction products are preferably not recirculated in the case of a tube reactor.

In the process of the invention, the reaction mixture preferably contains not more than 35% by weight of chloromethylsilane of the formula (I) and more preferably contains from 5 to 15% by weight of chloromethylsilane of the formula (I).

The starting materials chlorine and methylsilane of the formula (II) are preferably introduced into the reactor individually and exposed to the radiation without premixing. Hydrogen chloride is introduced individually into the reactor or may be premixed with the starting material methylsilane of the formula (II). Thus, hydrogen chloride can be premixed with methylsilane of the formula (II) to be chlorinated, recycled methylsilane containing hydrogen chloride from the work-up of crude product can be used, or a reaction mixture containing hydrogen chloride can be employed.

In the process of the invention, the starting materials and hydrogen chloride are preferably introduced concurrently into the photochemical reactor, more preferably in the absence of chlorinated reaction products or with exclusion of reaction mixture, i.e. by use of pure starting materials only.

The reaction is carried out at temperatures below the boiling point of the methylsilane of the formula (II), preferably in such a way that hydrogen chloride formed, due to its solubility in the reaction mixture, is released virtually completely in gaseous form in the reactor. The reaction temperature is adjusted by supplying an excess of methylsilane at a temperature significantly below its boiling point. Remaining hydrogen chloride is removed together with excess methylsilane of the formula (II) in the distillation of the reaction mixture.

In a preferred embodiment of the process of the invention, chlorine, which may be in gaseous or liquid form, and gaseous hydrogen chloride are introduced at a constant rate into a lower portion of a vertical tube reactor illuminated by means of a UV lamp, and an excess of the methylsilane of the formula (II) is also introduced into a lower portion of the reactor, at such a rate that the temperature of the reaction mixture remains below the boiling point of the methylsilane to be chlorinated. The UV lamp may be located outside the reaction tube or in the reaction tube, and the tube reactor is generally uncooled. The gas/liquid mixture leaving the tube reactor is then preferably separated into liquid and gaseous constituents in a receiving vessel or a cyclone.

The liquid reaction mixture obtained in the process of the invention, consisting for the most part of chlorinated methylchlorosilane of the formula (I) in which y=1 and a=1, unreacted silane of the formula (II), more highly chlorinated products, and hydrogen chloride corresponding to its solubility in the reaction mixture, can be subjected to separation processes known per se, for example by distillation in a column, in which case the desired product is then obtained in very pure form. The unreacted methylsilane of the formula (II) can be recirculated to the tube reactor together with hydrogen chloride which is not separated in the receiving vessel or cyclone.

If a loop reactor is employed in the process of the invention, liquid, degassed reaction mixture from the receiving vessel is preferably cooled and partly recirculated to the loop reactor.

Gaseous hydrogen chloride from the receiving vessel or cyclone is preferably reserved for another use.

The process of the invention is most preferably carried out employing a reactor in which a commercial, tubular, intermediate-pressure mercury vapor lamp having a protective quartz tube and a sheathing tube of borosilicate glass (e.g. Duran®) is installed concentrically in a metallic outer tube into which starting materials and hydrogen chloride flow from below so that the reactor is operated in a flooded state. When the process of the invention is carried out, hydrogen chloride formed at the glass surface of the UV lamp is advantageously released in gaseous form and consequently reduces the laminar boundary layer of the inflowing starting materials and thereby increases the utilizable radiation density of the UV lamp.

The present invention further provides an apparatus for preparing silanes containing chloromethyl groups under the action of electromagnetic radiation which induces chlorination, wherein a tubular intermediate-pressure mercury vapor lamp having a protective quartz tube and a sheathing tube of borosilicate glass (e.g. Duran®) is located within a metallic outer tube, preferably located concentrically within the outer tube, into which starting materials and hydrogen chloride flow from below so that the reactor is operated in a flooded state.

Examples of silanes of the formula (I) prepared by the process of the invention are $(ClCH_2)CH_3SiCl_2$, $(ClCH_2)(CH_3)_2SiCl$, $(ClCH_2)SiCl_3$, $(ClCH_2)(CH_3)_3Si$, $(ClCH_2)_2CH_3SiCl$ and $(Cl_2CH)(CH_3)_2SiCl$.

The process of the invention has the advantage that it can be carried out in a simple way with high operational safety margin. The process also has the advantage of saving energy by utilization of the heat of reaction for degassing and in the work-up of the reaction mixture by distillation. The process has the further advantage that no separate reactor cooling is required. In addition to the foregoing advantages, the process is advantageous in that silanes containing chloromethyl groups can be prepared at high conversion, which makes it possible for the chloromethylsilanes to be prepared economically on an industrial scale.

The apparatus of the invention has the advantage that it has a simple construction and can be operated in a simple manner. Furthermore, the apparatus has the advantage that it offers high operational safety, and no particular protective measures against high-energy radiation are necessary.

Unless indicated otherwise, the following examples are carried out at the pressure of the surrounding atmosphere, i.e. at about 1,000 hPa, and at room temperature, i.e. at about 23° C., or at a temperature which is established on combining the reactants at room temperature without additional heating or cooling. Furthermore, all parts and percentages are by weight unless indicated otherwise.

EXAMPLE 1

Preparation of Chloromethyltrichlorosilane (Silane CM)

A loop reactor having a 1 liter capacity is charged with 720 g of methyltrichlorosilane. 35 g of gaseous hydrogen chloride are introduced at a rate of 40 g/h into the methyltrichlorosilane.

The glass reaction tube of the loop reactor is illuminated from the outside by means of a UV lamp having a power of 40 watts and a wavelength range from 315 to 400 nm (UVA fluorescent lamp obtainable commercially under the trade name "Osram Eversun"). At the same time, 30 g of gaseous chlorine are introduced at a rate of 44 g/h into the lower end of the illumination section.

After introduction of 30 g of chlorine, 44 g/h of chlorine and 1,200 g/h of methyltrichlorosilane (20° C.) are metered continuously into the lower end of the illumination section.

The gas/liquid mixture leaving the illumination section (30° C.) separates in the downstream receiving vessel: gaseous hydrogen chloride leaves via the top, and liquid reaction mixture is drawn off via a siphon and is purified by distillation.

Liquid reaction mixture recirculated from the receiving vessel to the glass reaction tube is cooled to 20° C. prior to reintroduction into the reactor.

The product from the siphon comprises methyltrichlorosilane together with 5.0% of chloromethyltrichlorosilane and also 1.2% of dichloromethyltrichlorosilane and 0.7% of trichloromethyltrichlorosilane.

EXAMPLE 2

Preparation of Chloromethylmethyldichlorosilane (Silane CMM1)

A stream comprising 110 kg/h of liquid chlorine, 4.0 m³/h of dimethyldichlorosilane (30–33° C.) and 1.0 m³/h of gaseous hydrogen chloride is introduced continuously from below into the vertical tube reactor of VA steel (length, 1,850 mm; diameter, 200 mm) provided with an internally centrally integrated intermediate-pressure mercury vapor lamp (length, 1,450 mm; diameter, 150 mm) having a power of 4 kW and a predominant wavelength of 366 nm.

The illuminated gas/liquid mixture leaving the tube reactor (57° C.) is separated in a cyclone: hydrogen chloride leaves in gaseous form via the top, and liquid crude product flowing out at the bottom is passed to a continuous fractional distillation to give the individual components. The crude product from the cyclone comprises dimethyldichlorosilane together with 8.6% of chloromethylmethyldichlorosilane and 0.7% of dichloromethylmethyldichlorosilane. In the continuous distillation of crude product, the unreacted dimethyldichlorosilane is taken off at the top of the distillation column and fed back into the tube reactor. With the use of recycled dimethyldichlorosilane, the introduction of gaseous hydrogen chloride into the tube reactor is discontinued. Recycled dimethyldichlorosilane is supplemented with about 210 kg/h of fresh dimethyldichlorosilane to give a total of 4 m$^3$/h. The temperature at the top of the distillation column is 69° C., which corresponds to the boiling point of dimethyldichlorosilane. The temperature at the bottom in the steady state is 130° C. The product taken off continuously from the bottom (crude CMM1) has the following composition: 91.6% of chloromethylmethyldichlorosilane, 0.1% of dimethyldichlorosilane, 7.1% of dichloromethylmethyldichlorosilane, and 1.2% of higher-boiling by-products. 245 kg/h of crude CMM1 are obtained. The total yield of pure product based on chlorine used is thus 96.6%. Crude CMM1 is purified by distillation via a column. Chloromethylmethyldichlorosilane is obtained as main fraction in purities of above 99.0%.

EXAMPLE 3

Preparation of Chloromethyldimethylchlorosilane (silane CMM2)

The preparation is carried out by a method analogous to example 2. 110 kg/h of liquid chlorine, 5.0 m$^3$/h of trimethylchlorosilane (30° C.) and 1.0 m$^3$/h of gaseous hydrogen chloride are introduced continuously from below into the tube reactor provided with an integrated intermediate-pressure mercury vapor lamp, as described in more detail in example 2. With the use of recycled trimethylchlorosilane from the distillation, hydrogen chloride addition is stopped. Recycled trimethylchlorosilane obtained in the distillation is supplemented with about 190 kg/h of fresh trimethylchlorosilane to give a total of 5.0 m$^3$/h.

The temperature at the reactor outlet is 48° C. Crude product from the cyclone comprises trimethylchlorosilane together with 10.2% of chloromethyldimethylchlorosilane and 0.7% of more highly chlorinated silanes.

The product taken off continuously from the bottom of the distillation (crude CMM2) has the following composition: 95.5% of chloromethyldimethylchlorosilane, 0.1% of trimethylchlorosilane, 2.7% of dichloromethyldimethylchlorosilane, and 1.7% of higher-boiling by-products.

220 kg/h of crude CMM2 are obtained. The total yield of pure product based on chlorine used is thus 94.6%. Crude CMM2 is purified by distillation via a column. Chloromethyldimethylchlorosilane is obtained as main fraction in purities of above 99.0%.

EXAMPLE 4

Preparation of Chloromethyldimethylchlorosilane (Silane CMM2)

A loop reactor having a 2.5 liter capacity is charged with 2.0 kg of trimethylchlorosilane. 35 g of gaseous hydrogen chloride are introduced at a rate of 40 g/h into the trimethylchlorosilane.

The glass reaction tube of the loop reactor is illuminated from the outside by means of a UV lamp having a power of 40 watts and a wavelength range from 315 to 400 nm (UVA fluorescent lamp obtainable commercially under the trade name "Osram Eversun"). At the same time, x mol % of gaseous chlorine (based on 2.0 kg of trimethylchlorosilane) are introduced at a rate of 88 g/h into the lower end of the illumination section, where x is as shown in table 1.

After introduction of x mol % of chlorine, x mol % of chlorine/h and 625 g/h of trimethylchlorosilane (20° C.) are metered continuously into the lower end of the illumination section.

TABLE 1

| | | Composition of the reaction mixture | | |
|---|---|---|---|---|
| Chlorine input | | | Chloro- | |
| x mol % of chlorine based on trimethyl-chloro-silane used | g chlorine/h | Tri-methyl-chloro-silane | methyl-dimethyl-chloro-silane | Sum of more highly chlorinated silanes |
| 9.4 | 37 | 88.0 | 9.2 | 2.8 |
| 18.9 | 77 | 78.4 | 16.9 | 4.7 |
| 28.3 | 115 | 71.2 | 22.1 | 6.7 |
| 37.7 | 154 | 65.6 | 26.2 | 8.2 |
| 47.2 | 193 | 55.5 | 32.6 | 11.9 |

The gas/liquid mixture leaving the illumination section (30° C.) separates in the downstream residence vessel: gaseous hydrogen chloride leaves via the top, and liquid reaction mixture is taken off via a siphon and is purified by distillation. In addition to chloromethyldimethylchlorosilane, dichloromethyldimethylchlorosilane and bis(chloromethyl)methylchlorosilane are obtained in purities of at least 98% and 96%, respectively.

Liquid reaction mixture recirculated from the residence vessel to the glass reaction tube is cooled to 20° C. prior to reintroduction into the reactor.

EXAMPLE 5

Preparation of Chloromethyldimethylchlorosilane (Silane CMM2)

A loop reactor having a 27 liter capacity is charged with 23 kg of trimethylchlorosilane. 1.5 kg of gaseous hydrogen chloride are introduced at a rate of 2 kg/h into the trimethylchlorosilane.

The glass reaction tube of the loop reactor is illuminated from the outside by means of a UV lamp having a power of 120 watts and a wavelength range from 315 to 400 nm (UVA fluorescent lamp obtainable commercially under the trade name "Osram Eversun"). At the same time, 3.75 kg of gaseous chlorine are introduced at a rate of 18 kg/h into the lower end of the illumination section. After introduction of 3.75 kg of chlorine, 18 kg of chlorine/h and 103 kg/h of trimethylchlorosilane (−10° C.) are metered continuously into the lower end of the illumination section.

The temperature at the end of the illumination section is 36° C. The gas/liquid mixture leaving the illumination section separates in the downstream receiving vessel: gaseous hydrogen chloride leaves via the top, and liquid reaction mixture is drawn off via a siphon and is purified by distillation.

Liquid reaction mixture recirculated in the circuit from the residence vessel to the glass reaction tube is cooled to 20° C. prior to reintroduction into the reactor.

Degassed reaction mixture from the residence vessel comprises unreacted trimethylchlorosilane together with 23.9% by weight of chloromethyldimethylchlorosilane and also 3.3% of dichloromethyldimethylchlorosilane and 2.7% of more highly chlorinated silanes.

The work-up of the reaction mixture is carried out by continuous or batchwise fractional distillation at atmospheric pressure. Unreacted trimethylchlorosilane obtained as first fraction is reused in the chlorination without further purification. Chloromethyldimethylchlorosilane is obtained as main fraction in purities of above 99.0% by weight.

EXAMPLE 6

Preparation of Chloromethyltrimethylsilane (Silane CMM3)

A loop reactor having a 1 liter capacity is charged with 630 g of tetramethylsilane. 30 g of gaseous hydrogen chloride are introduced at a rate of 40 g/h into the tetramethylsilane.

The glass reaction tube of the loop reactor is illuminated from the outside by means of a UV lamp having a power of 18 watts and a wavelength range from 400 to 800 nm (UVA fluorescent lamp obtainable commercially under the trade name "Osram Fluora-Strahler"). At the same time, 86 g of gaseous chlorine are introduced at a rate of 34 g/h into the lower end of the illumination section.

After introduction of 86 g of chlorine, 34 g/h of chlorine and 250 g/h of precooled tetramethylsilane (−10° C.) are metered continuously into the lower end of the illumination section.

The temperature at the end of the illumination section is from 0° C. to 1° C. The gas/liquid mixture leaving the illumination section separates in the downstream receiving vessel: gaseous hydrogen chloride leaves via the top, and liquid reaction mixture is taken off via a siphon and is purified by distillation.

Liquid reaction mixture recirculated in the circuit from the residence vessel to the glass reaction tube is cooled to −10° C. prior to reintroduction into the reactor.

Degassed reaction mixture from the residence vessel comprises unreacted tetramethylsilane together with 7.2% by weight of chloromethyltrimethylsilane and 2.2% of more highly chlorinated silanes.

The work-up of the reaction mixture is carried out by continuous or batchwise fractional distillation at atmospheric pressure. Unreacted tetramethylsilane obtained as first fraction is reused in the chlorination without further purification.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing silanes which contain chloromethyl groups and have the formula $$(Cl_yCH_{3-y})_a(CH_3)_bSiCl_{4-a-b}$$

where y is 1, 2 or 3, a is 1, 2, 3, or 4, b is 0, 1, 2 or 3, with the proviso that the sum a+b is 1, 2, 3 or 4, which comprises reacting methylsilanes of the formula $$(CH_3)_{a+b}SiCl_{4-(a+b)} \qquad (II),$$

with chlorine in the presence of at least 0.1% by weight of hydrogen chloride, based on the weight of methylsilane of the formula (II), under the action of electromagnetic radiation which promotes chlorination, chlorine present in a substoichiometric amount based on the methylsilane of the formula (II), and the reaction carried out at temperatures below the boiling point of the methylsilane of the formula (II).

2. The process of claim 1, wherein hydrogen chloride is present in an amount of at least 0.2% by weight based on the weight of methylsilane of the formula (II).

3. The process of claim 1, wherein the molar ratio of methylsilane of the formula (II) to chlorine is above 2.0:1.0.

4. The process of claim 1, which is carried out at a temperature from 5 to 15° C. below the boiling point of the methylsilane of the formula (II) and at the pressure of the surrounding atmosphere.

5. The process of claim 1, wherein said process is a continuous process.

6. The process of claim 5, wherein said continuous process takes place in a tube reactor or a loop reactor.

7. The process of claim 1, wherein chlorine in gaseous or liquid form, and gaseous hydrogen chloride are introduced at a constant rate into a lower portion of a vertical tube reactor illuminated by means of a UV lamp, an excess of the methylsilane of the formula (II) is introduced into a lower portion of said vertical tube reactor at such a rate that the temperature of the reaction mixture remains below the boiling point of the methylsilane to be chlorinated, the tube reactor being uncooled.

8. The process of claim 7, wherein said UV lamp is positioned within the tube reactor.

9. The process of claim 1, wherein an outlet stream comprising unreacted methylsilane of the formula II and hydrogen chloride is cooled and recirculated as a recycle feed stream to the reactor, the amount of gaseous hydrogen chloride introduced into said reactor being reduced proportionately with the amount of hydrogen chloride in said recycle feed stream.

* * * * *